United States Patent
Monson et al.

(10) Patent No.: US 8,471,088 B2
(45) Date of Patent: Jun. 25, 2013

(54) SOLVENT QUALITY CONTROL IN EXTRACTION PROCESSES

(75) Inventors: John Joseph Monson, League City, TX (US); Arnold Hee-Sur Choi, Houston, TX (US); Dana Lynn Pilliod, League City, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 13/345,455

(22) Filed: Jan. 6, 2012

(65) Prior Publication Data

US 2012/0197057 A1 Aug. 2, 2012

Related U.S. Application Data

(60) Provisional application No. 61/437,802, filed on Jan. 31, 2011.

(51) Int. Cl.
*C07C 7/17* (2006.01)

(52) U.S. Cl.
USPC .................. 585/833; 585/857; 585/865

(58) Field of Classification Search
None
See application file for complete search history.

(56) References Cited

U.S. PATENT DOCUMENTS

| | | | |
|---|---|---|---|
| 2,878,182 A | 3/1959 | Bloch | |
| 3,720,605 A | 3/1973 | Paret et al. | |
| 7,288,184 B2 | 10/2007 | Van Nuland et al. | |
| 2006/0124509 A1 | 6/2006 | Van Nuland et al. | |
| 2010/0096321 A1 | 4/2010 | Monson | |

FOREIGN PATENT DOCUMENTS

FR 2079236 11/1971

*Primary Examiner* — Tam M Nguyen
(74) *Attorney, Agent, or Firm* — Andrew B. Griffis

(57) ABSTRACT

The invention concerns the control of solvent systems in processes and apparatus for the separation of aromatic hydrocarbons from non-aromatic hydrocarbons in liquid-liquid extraction, extractive distillation, and the combination thereof.

6 Claims, 3 Drawing Sheets

SOLVENT QUALITY CONTROL IN EXTRACTION PROCESSES

PRIORITY CLAIM

This application claims priority to U.S. Provisional Application Ser. No. 61/437,802 filed Jan. 31, 2011, the disclosure of which is fully incorporated herein by reference.

BACKGROUND OF THE INVENTION

1. Field of the Invention

The present invention relates to hydrocarbon separation, and more particularly to liquid-liquid solvent extraction, vapor-liquid solvent extraction (also known as extractive distillation) and a system adapted for the practice thereof.

2. Description of the Related Art

Aromatic hydrocarbons, such as benzene, toluene and xylenes (collectively, "BTX"), serve as important building blocks for a variety of plastics, foams and fibers. Often these compounds are produced via catalytic reformation of naphtha through steam cracking of naphtha or gas oils, or other methods where substantial amounts of non-aromatic compounds are present. When simple distillation or fractionation is not a cost effective or practical method for separation, liquid-liquid extraction or vapor-liquid extraction techniques are used. Such extraction techniques separate a desired substance selectively from a mixture or remove unwanted impurities from solution, and, in the present context of aromatic hydrocarbon separation from non-aromatic hydrocarbons, typically use a solvent which exhibits a higher affinity for the aromatic compounds than the non-aromatic compounds, thereby selectively extracting the aromatic compounds from the mixture of aromatics and non-aromatics. The aromatic species of interest can then be isolated from the solvent by distillation, adsorptive separation techniques, and the like.

One widely used solvent extraction technique is the Sulfolane™ process developed by UOP, which is discussed in numerous patents and other literature too numerous to cite. The process uses a combination of liquid-liquid extraction and extractive distillation in a single, integrated design, and employs tetrahydrothiophene-1,1-dioxide (or sulfolane) as a solvent and water as a co-solvent. One of the problems with this process is that light impurities have a tendency to buildup in the system, such as in one or more distillation towers and recycle streams. Without wishing to be bound by theory, this may be due at least in part to sieve tray fouling or high unit rates, both reducing disengaging times. These undesired effects result in the incapacity of the extractor to efficiently remove and recover the aromatic compounds within the mixed feedstock and may also lead to leaks due to corrosion, the latter of which may have catastrophic results.

Other solvents conventionally used in liquid-liquid extraction include oxygen-containing species such as tetraethylene glycol and nitrogen-containing species such as N-methylpyrrolidine, each having similar issues, as well as their own unique problems, that lead to decreasing the capacity of the extraction process.

Typical responses to correcting the incapacity of the extractor include one or more of moving the recycle location, adding more stages of sieved trays, reducing operating rates, or cleaning and/or replacing the sieve tray decks. Numerous other solutions have been disclosed, such as in U.S. Pat. No. 7,288,184, and U.S. Publication 2010-0096321. Other references of interest include U.S. Pat. Nos. 7,288,184; 3,720,605; and 2,878,182; and FR 2079236.

The present inventors have discovered that proper control of the solvent systems in the separation of aromatic hydrocarbons from non-aromatic hydrocarbons, including liquid-liquid extraction processes and extractive distillation processes, and the combination thereof, can result, in embodiments, in at least an order of magnitude improvement in reliability and integrity of the solvent systems and processes for the separation of aromatic hydrocarbons and non-aromatic hydrocarbons.

SUMMARY OF THE INVENTION

The invention concerns the control of solvent systems in processes and apparatus for the separation of aromatic hydrocarbons from non-aromatic hydrocarbons in liquid-liquid extraction, extractive distillation, and the combination thereof.

In embodiments, the invention concerns a systematic quality control program that includes control of free oxygen and organic-chlorides in the feed stream, solvent and water systems used in liquid-liquid extraction or extractive distillation processes and apparatus adapted therefor. In preferred embodiments, control of ingress of oxygen and organic chlorides into these liquid-liquid extraction processes can result in an order of magnitude improvement in quality and long-term reliability of said systems.

It is an object of the invention to maintain long-term solvent stability (and therefore the quality) by preventing the formation of unwanted by-products, including polymers and organic acids, resulting in corrosion of materials such as carbon steel and associated equipment fouling.

These and other objects, features, and advantages of the present invention will become apparent in the following detailed description, drawings, specific embodiments, experiments, and claims.

BRIEF DESCRIPTION OF THE DRAWINGS

In the accompanying drawings, like reference numerals are used to denote like parts throughout the several views.

DETAILED DESCRIPTION

Figure 1:
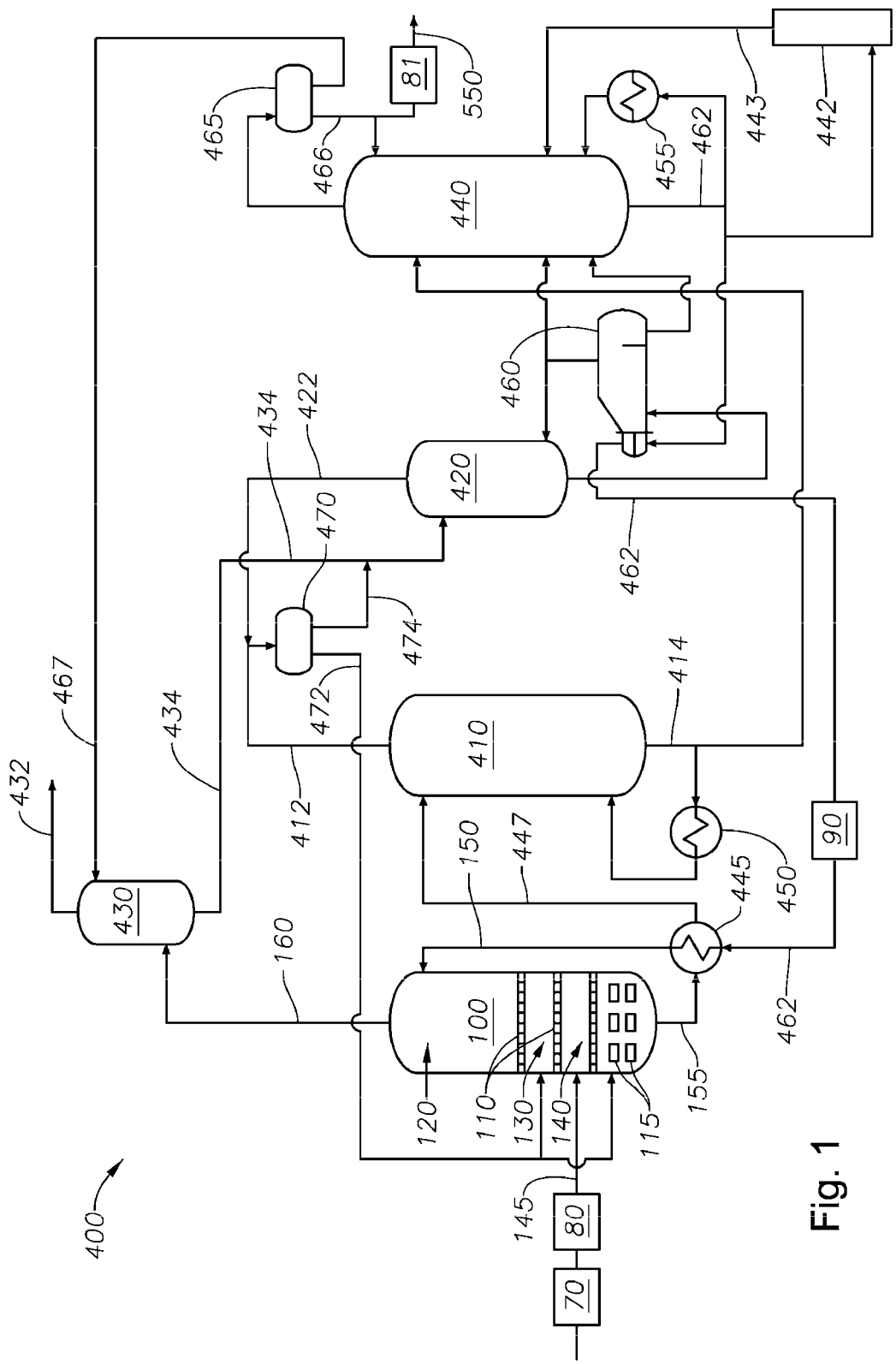
FIG. 1 depicts a schematic view of an embodiment of an extraction system for separating a hydrocarbon, according to the present invention.

The invention concerns an improvement in the long term reliability of solvent systems used in liquid-liquid extraction (LLE) or extractive distillation (ED) techniques, and combinations thereof, for the separation of aromatic hydrocarbons from non-aromatic hydrocarbons.

In embodiments, the amount of free, molecular oxygen ($O_2$) in the feed is kept below 0.1 vppm (per liter solvent), preferably less than 0.02 vppm, and the amount of organic chlorides in the feed is kept below 0.1 wppm (per kilogram solvent), as chloride. Organic chloride (or organo chloride) as used herein means a hydrocarbon species having a chloride directly bonded to carbon, for example propylchloride or butylchloride. The hydrocarbon species may contain other heteroatoms, e.g., oxygen, nitrogen, and the like.

In embodiments, the amount of free, molecular oxygen in the equipment vapor phase of the LLE or ED system is less than 500 wppm prior to inventorying the unit and preparing for start-up.

The amount of oxygen may be determined by standard equipment per se known in the art and the amount of chloride may be determined by ASTM D-7536.

In embodiments, TAN value of the solvent, is maintained less than 1 meq/L. As per se known in art, Total Acid Number, or TAN, is considered a measure of the acid content of a sample. High Total Acid Number (TAN) crudes are typically much less valuable than crudes that do not have high acid concentrations. Ordinarily TAN measures free acid, however in accordance with the present invention TAN measures total acid concentration, including both free acid and salts. There are several methods for measuring TAN and the particular method is not important, except that both free acids and acid salts must be accounted for in the measurement. One of ordinary skill in the art, in possession of the present disclosure, can modify known methods so as to include both free acid in the sample and also include acid salts.

Qualitatively, when TAN, measured according to the present invention, begins to increase, the system becomes harder to operate and/or separation of product becomes more difficult. It then becomes time to change out the regenerator system, element 442 in FIG. 1, described in more detail below, with fresh material and/or to remove build up of particles, and the like.

In embodiments, the amount of chloride ions in the aromatics extraction unit system should be kept less than 25 wppm, based on Cl$^-$.

In embodiments, pH of the solvent shall be kept between 6-9, preferably between 6.5 and 8.0. The pH of the water shall be maintained between 6-10, preferably between 7-9.

In embodiments, the circulating solvent particulates shall be maintained less than 5 microns, or less than 1.0 microns, but preferably less than 0.5 microns. A minimum volume of circulating solvent filtering is specified. The present inventors have found that without this specification, an increase in pressure change across the system begins to raise after about 6 months. When pressure does begin to raise, it is time to change out the filter materials. A convenient location for filtering can be element 90 in FIG. 1, but again this is merely representative and additional and/or alternate locations may be selected by one of ordinary skill in the art.

Maintaining solvent quality specifications is achieved in various ways.

Solvent and water pH is controlled via periodic injection of a base, e.g. MEA (mono-ethanolamine) of DEA (di-ethanolamine). It is highly advantageous to maintain historical monitoring of the required neutralization volumes to maintain unit pH to look for performance trends. The base is preferentially added to the reboiler inlet of the stripper tower (discussed in detail with respect to FIG. 1, below) but may instead or in addition be added at one or more of the water to the raffinate wash column, rich solvent from the extractor tower, recovery column, extractor feed, and the like. Condensate make-up preferentially also has an amine package added, which may advantageously contain morpholine, which can be added conveniently to the recovery column overhead.

Figure 2:
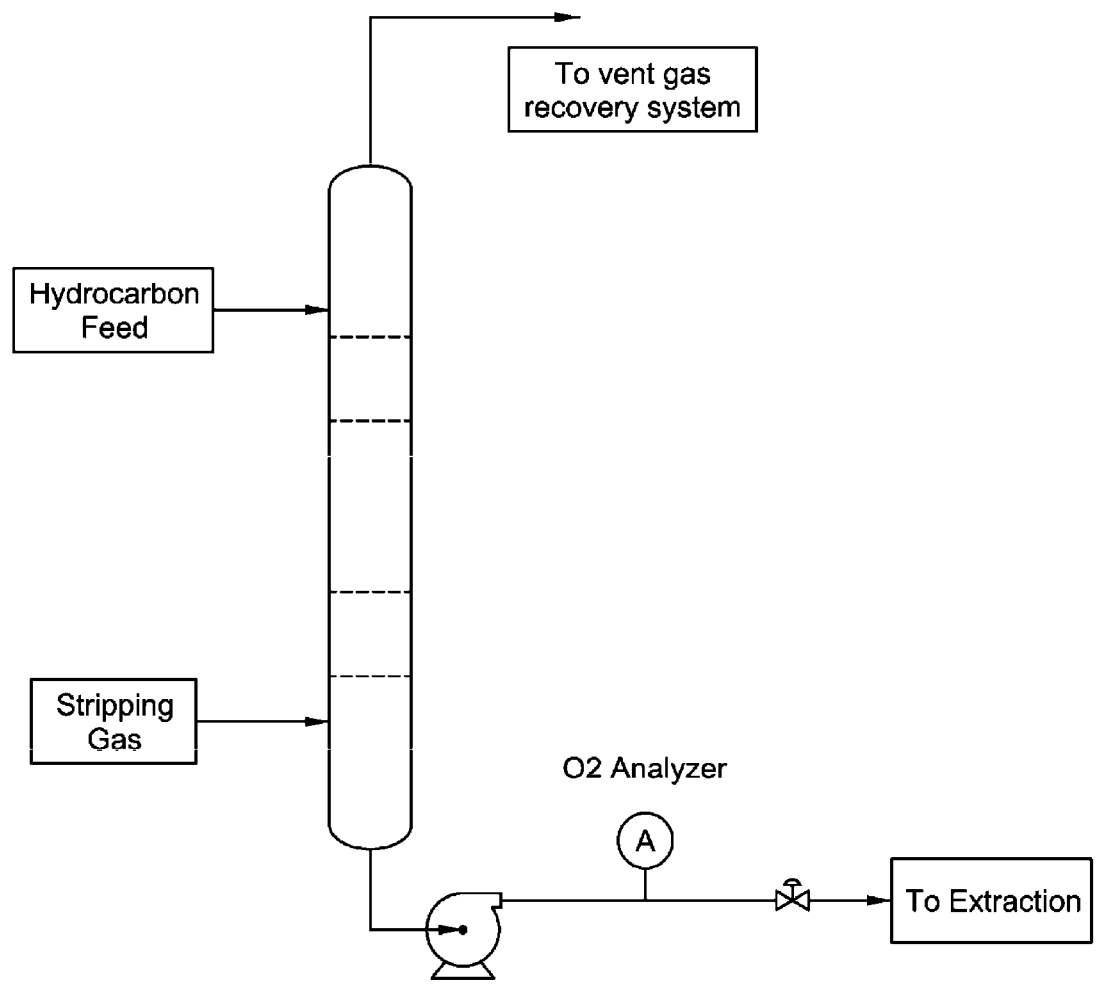
FIG. 2 depicts a schematic view of an embodiment of a system for separating dissolved oxygen from a hydrocarbon stream according to the present invention.

There are two methods that are typically employed for removing dissolved, molecular oxygen, from extraction unit feed, either heat soaking or gas stripping. FIG. 2 shows a gas stripper design useful in the present invention. Hydrocarbon is fed to nominally the middle or upper section of a tower, as shown in FIG. 2, containing contacting internals, illustrated by the dotted lines within said tower. Stripping gas, typically, hydrogen, nitrogen, or natural gas, is introduced near the bottom of the tower, as shown in FIG. 2. The hydrocarbon flows down the tower while the gas moves up the tower displacing the $O_2$ dissolved in the hydrocarbon. Outlet dissolved $O_2$ analyzers, of the type per se known in the art, are employed to ensure oxygen removal to below specifications. Off gas overhead is typically sent to a fuel gas recovery system and the de-oxygenated hydrocarbon feed enters the extraction system.

On line oxygen analyzers can also be installed on the aromatics product, or extract, from the extraction unit. These analyzers detect vacuum leaks associated with the recovery column and associated equipment. Accordingly, they can be placed in one or more locations to isolate source(s) of leaks and maintain solvent quality.

Figure 3:
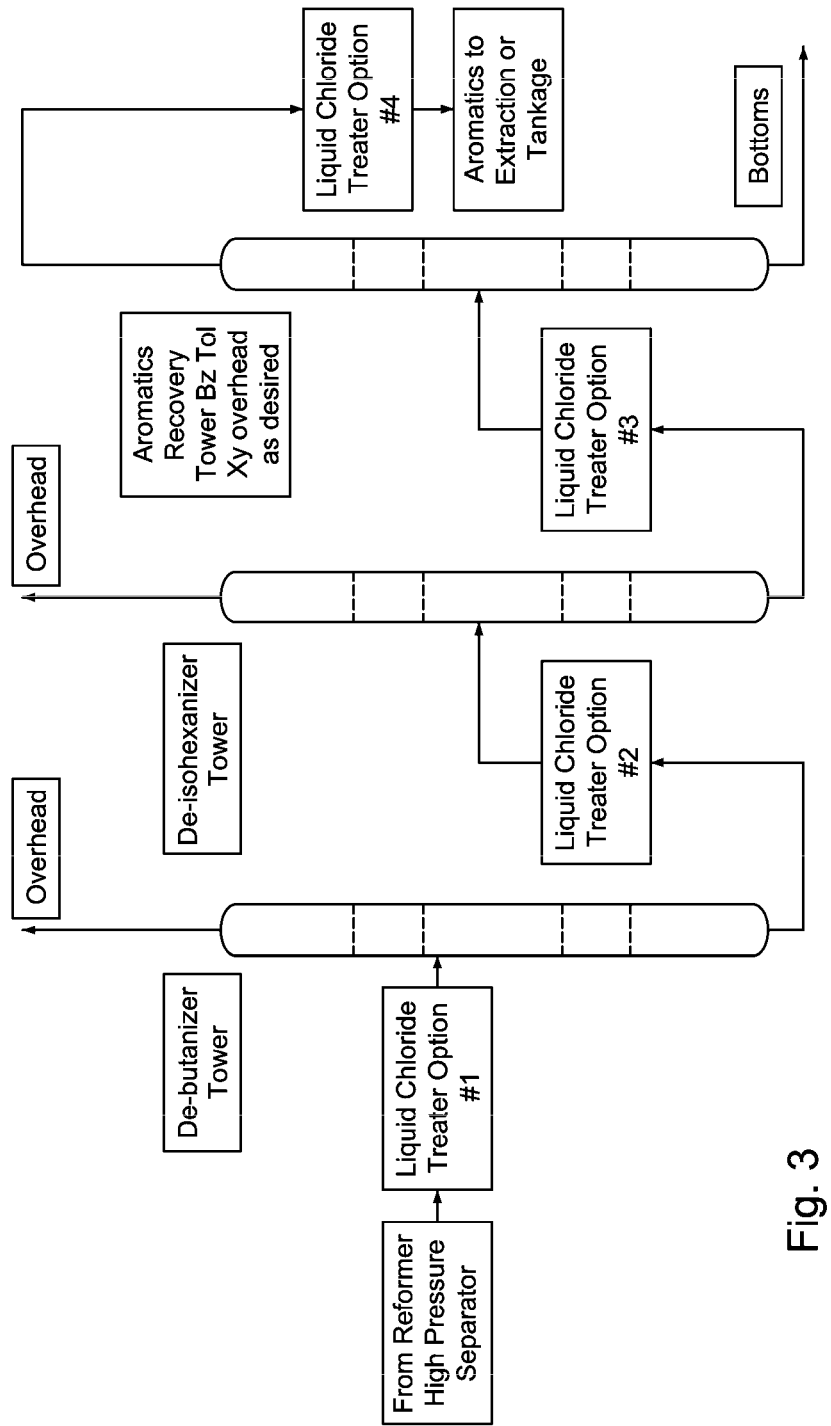
FIG. 3 depicts a schematic view of an embodiment of a system for separating chloride (organic and inorganic) from a hydrocarbon stream.

Chlorides in the feed hydrocarbon can be adsorbed using industry methods. Typically chloride adsorption is done in the off gas from a reformer. As these adsorbers become loaded with chloride, side reactions occur creating organo-chlorides. These organo-chlorides then enter the benzene fraction via a recontacting drum. FIG. 3 shows one such system for introducing a chloride adsorption bed into a typical reformate stream and removing organochlorides prior to introduction to the extraction system. As illustrated schematically in FIG. 3, one or more liquid chloride treaters can be used at various locations, for example; upstream of the stabilizer/debutanizer tower, but more frequently used upstream of the deisohexanizer, the benzene splitter, or resulting reformate stream to an extraction unit.

Particulates are removed via circulating, lean solvent filters. Additionally, various interface layers in the LLE or ED equipment can be filtered and returned to the extractor. Filter elements are typically wound fiberglass, but can be made of many other materials. Filters are supplied by various manufacturers. A convenient location is shown by element 90 in FIG. 1, however this is used for illustrative purposes only and different or additional locations may be used. The present inventors have found that element size is important to maintain long term stability. The filter elements should be no greater than 1.0 micron diameter, preferably 0.5 microns in diameter.

Solvent regeneration equipment is used to improve the solvent quality due to routine solvent degradation or due to poor quality management practices. There are various types of equipment employed but steam assisted vacuum regeneration, of the type per se known in the art, is preferred. Other solvent regeneration equipment methods include; adsorption by alumina or ion exchange resins such as disclosed in U.S. Pat. No. 7,288,184.

Terms such as "aromatic hydrocarbons", "aliphatic hydrocarbons", and "solvent" are per se well-known in the art and take their ordinary meaning. Reference should be made to the prior art discussed in the background when in doubt.

This invention is applicable to processes in which mixtures of aromatic and aliphatic (including cycloaliphatic) hydrocarbons are separated by extraction of the aromatic hydrocarbons and stripping the aromatic hydrocarbons from the extracting solvent. The hydrocarbons can have from 4 to 12 carbon atoms and preferably have 6 to 8 carbon atoms in commercially more important embodiments.

The UOP Sulfolane™ process is a liquid-liquid extraction process to recover high-purity aromatics from hydrocarbon mixtures, such as reformate, pygas, or coke-oven light oil. This process is described, for instance, in the Handbook of Petroleum Refining Process, 2nd edition (1996) p. 2.13.

The extracting solvent is any liquid that preferentially extracts aromatic hydrocarbons over aliphatic hydrocarbons.

The boiling point of the extraction solvent should be higher than the boiling point of the aromatic hydrocarbons being extracted (i.e., it should have a boiling point of at least 100° C. and preferably between about 200° C. and about 300° C.) so that it is not evaporated during stripping. In embodiments, the preferred extracting solvent is Sulfolane™, available as Sulfolane W® from Phillips Chemical Company, Bartlesville, Okla., USA. In other embodiments the solvent is selected from glycols, such as di-, tri-, and tetraethylene glycol, and nitrogen-containing species such as N-methylpyrrolidine. Mixtures of such solvents can be used.

The present inventors have discovered that systematically and proactively minimizing free oxygen and organic-chlorides from the extraction processes provides, in embodiments, an order of magnitude improvement in reliability and integrity of solvent systems. Without wishing to be bound by theory, elimination or minimization of free oxygen, and organic chlorides prevents formation of unwanted by-products, including polymers, inorganic acids, and organic acids resulting in corrosion of carbon steel and associated equipment fouling.

Organic chlorides in an aromatics extraction unit will rapidly thermally decompose, in the presence of Sulfolane™, to species such as hydrochloric acid and an olefin. The hydrochloric acid will result in a decrease in the pH of the Sulfolane™ and/or water circuits resulting in accelerated unit corrosion rates.

Poor solvent quality impacts all aspects of aromatics extraction operations including, capacity availability, mechanical reliability, turnaround average availability, and variable operating costs. Poor solvent quality can cause loss of extraction unit capacity due to poor phase separation in liquid/liquid extraction (emulsions) and foaming in downstream fractionation. In the most extreme cases, corrosion from degradation by products can be severe enough to cause an unscheduled shut down of the extraction unit and/or result in adverse benzene exposure to personnel and the environment.

All inlet streams to the extraction unit shall be less than 1 vppm free oxygen as measured with a portable Orbisphere analyzer or an on-line Metler Toledo analyzer. All inlet streams to the extraction unit shall maintain less that 0.1 vppm free oxygen.

Analyzers for dissolved $O_2$ are commercially available. The Metler Toledo™ corporation manufactures on-line dissolved $O_2$ analyzers that can be used for feed streams according to the present invention. The Orbisphere™ Company manufactures a portable analyzer that can be used for free oxygen analysis in hydrocarbon streams. These same analyzers can also be used for vapor analyses.

Air and nitrogen are used as the standards for calibration. On-line analyzer calibration curves are then translated to the saturated dissolved oxygen curves for a specific hydrocarbon stream concentration. The analyzer gain is adjusted to range the 4-20 mA analyzer output signal to correspond to a 0-10 ppm $O_2$ scale. This improves the low end sensitivity and reproducibility of the analyzer. The 4-20 mA output signal is then transferred to a computer based DCS (digital control system). All inlet streams to the aromatics extraction unit shall have less than 1 vppm free oxygen, preferably, less than 0.1 vppm dissolved, free oxygen. Routine monitoring has shown typical feed concentrations of <0.015 vppm dissolved $O_2$ may be obtained without undue experimentation by one of ordinary skill in the art in possession of the present disclosure.

In embodiments, the recovery column extract analyzer is set up the same way. The oxygen in the extract is monitored to ensure no vacuum leaks on the recovery column or associated equipment. The extract is monitored for dissolved $O_2$ at a spec of 1.0 vppm max, or more preferably less than 0.1 vppm $O_2$, or typically less than 0.02 15 vppm $O_2$. If $O_2$ rises above the selected value, the source of the leak is determined and the leak is fixed. Constant vigilance in this regard, in combination with solvent purity with respect to chloride concentration, as described elsewhere herein, makes the difference between an extractor system which exhibits corrosion problems within months, if not weeks, and a system which can operate for a decade or longer, according to the projections and experience of the present inventors.

In the case of a feed comprising catalytically cracked reformate (CCR reformate), it is preferred to maintain less than 0.4 wppm (as Chloride) organic-chlorides in the feed to liquid-liquid extraction units and less than 0.1 wppm (as Chloride) in the feed to extractive distillation units. These are maximum specifications. Typical chloride levels in extraction unit feeds are <0.1 wppm.

Various methods can be used for chloride detection. For instance, precise and accurate measurements can be made using a sample concentrator, followed by acid digestion, and detection of the species of interest by ion chromatography or plasma. ASTM D-7536 can also be used to a detection limit around 0.06 wppm chloride.

Chlorides in circulating solvent should be maintained below 25 wppm but preferably less than 5 wppm. However, chloride concentrations should be maintained below the 25 wppm due to its ability to promote degradation of the extraction solvent, e.g., Sulfolane™, in the presence of oxygen and high temperatures. Bulk sulfolane temperatures should be maintained less than 199° C. (390° F.), or less than 188° C. (370° F.), but preferably less than 182° C. (360° F.). In still other embodiments, for instance when BTX components are desired as extract, the bulk sulfolane temperature may be kept no higher than 160° C. (320° F.) or when BT components are desired as extract the bulk sulfolane temperature may be kept no higher than 154° C. (310°). Heat exchanger skin temperatures shall be maintained less than 260° C. (500° F.), in embodiments less than 249° C. (480° F.), and in more preferred embodiments less than 238° C. (460°).

A further understanding of the invention can be realized by reference to FIG. 1, which per se illustrates a schematic according to the prior art, but which, however, can be used to also illuminate the present invention. In conjunction with FIGS. 2 and 3 and the present disclosure. It will be understood by one of ordinary skill in the art in possession of the present disclosure that certain valves, pumps, condensers, and the like, are not shown for convenience of view.

FIG. 1 depicts a schematic view of an illustrative system 400 for separating a hydrocarbon, according to one or more embodiments described. In addition to one or more liquid-liquid extractor unit(s) 100 described above, the system 400 can further include one or more extractive distillation units (or strippers) 410, water strippers 420, water wash columns 430, and recovery columns 440. In one or more embodiments, the system 400 can further include one or more heat exchangers (three are shown 445, 450, 455), one or more steam generators 460, and one or more water/hydrocarbon separators (two are shown 465, 470).

The feed to the system 400 is first introduced to a chloride stripper 70, illustrated by the preferred embodiments shown in FIG. 3, described in detail hereinbelow, and then to a deaeration tower 80, illustrated by the preferred embodiment shown in FIG. 2. The order of the chloride stripper 70 and deaeration tower 80 can be reversed, but the configuration shown in FIG. 1 is preferred. Within the extractor 100, a hydrocarbon mixture via line 145 (entering the extractor 100 at one or more locations) and a circulating solvent via line 150 can be contacted or otherwise mixed with one another. According to the present invention, it is the feed entering the extraction unit via line 145 and the circulating solvent in line 150 and elsewhere that take the values with respect to TAN, free molecular oxygen, organic chloride content, and chloride content, as Cl⁻, previously described. One of ordinary skill in the art in possession of the present disclosure can determine the number and placement such measuring devices or sample measurements as needed, other than as shown in FIG. 1. The solvent extracts or otherwise separates at least a portion of the aromatic hydrocarbons from the multi-component hydrocarbon introduced via line 145 to provide a solvent enriched in aromatic hydrocarbons ("rich solvent") via line 155 and a raffinate having a reduced content of aromatic hydrocarbons via line 160.

The solvent can include any suitable material suitable for separating aromatic compounds from non-aromatic compounds. Illustrative solvents can include, but are not limited to tetraethylene glycol, triethylene glycol, diethylene glycol, ethylene glycol, methoxy triglycol ether, diglycolamine, dipropylene glycol, N-formyl morpholine, N-methyl pyrrolidone, 2,3,4,5-tetrahydrothiophene-1,1-dioxide ("sulfolane"), 3-methylsulfolane and dimethyl sulfoxide, tetramethylene sulfone, alone and/or in admixtures with water, and/or in combination with each other and/or water. In one or more embodiments, the solvent can have a pH ranging from a low of about 5, about 5.5, or about 6 to a high of about 8, about 8.5, or about 9. For example, the pH of the solvent in line 150 can range from about 5 to about 9, or about 5.5 to about 8, or about 6 to about 7.

The hydrocarbon feed via line 145 can be or include a mixture of aromatics and non-aromatics. Typical, aromatics can include one or more $C_6$-$C_9$ aromatic hydrocarbons, including benzene, toluene, and/or xylene. In one or more embodiments, the hydrocarbon feed can be or include a product stream from catalytically reformed naphthas in which a $C_9$ cut or extract of the reformate is enriched in $C_9$ alkylbenzenes. A typical composition of such $C_9$ cut can contain about 2.5% mol $C_8$, 87.5% mol $C_9$ and 10% mol $C_{10}$ aromatics. In one or more embodiments, the hydrocarbon feed can be or include $C_6$-$C_9$ aromatic hydrocarbons derived from gasoline producing processes such as the conversion of methanol to gasoline, as described in U.S. Pat. Nos. 3,931,349; 3,969,426; 3,899,544; 3,894,104; 3,904,916; and 3,894,102, and/or the conversion of synthesis gas to gasoline as described in U.S. Pat. Nos. 4,096,163; 4,279,830; 4,304,871; and 3,254,023. In one or more embodiments, the hydrocarbon feed can be or include $C_6$-$C_9$ mixed aromatic hydrocarbons such as those derived from petroleum refinery sources, pyrolysis of coal to produce coke, tar sands, etc. In one or more embodiments, the hydrocarbon feed can be or include an alkylaromatic stream from a transalkylation, isomerization, and/or disproportionation operation.

In one or more embodiments, the volumetric solvent to hydrocarbon feed (S:H) ratio can range from about 1:1, to about 5:1, or from about 1:1 to about 3:1, or from about 1:1 to about 2:1. In at least one specific embodiment, the S:H ratio can be about 1.5:1. In one or more embodiments, the solvent in line 150 can be introduced to the extractor 100 at a temperature ranging from a low of about 40° C., about 50° C., or about 60° C. to a high of about 80° C., about 95° C., or about 100° C. For example, the temperature of the solvent in line 150 can range from about 60° C. to about 85° C.

In one or more embodiments, the extractor 100 can be operated at a pressure ranging from a low of about 225 kPa-g, about 250 kPa-g, or about 275 kPa-g to a high of about 400 kPa-g, about 450 kPa-g, or about 500 kPa-g. The extractor 100 can be operated at a temperature ranging from about 40° C., about 50° C., or about 60° C. to a high of about 70° C., about 85° C., or about 100° C. In at least one specific embodiment, the extractor 100 is operated at a temperate of from about 50° C. to about 70° C.

The rich solvent in line 155 can have a hydrocarbon concentration ranging from a low of about 10% wt, about 15% wt, or about 20% wt to a high of about 30% wt, about 35% wt, or about 49% wt, with the balance being the solvent. Of the hydrocarbons in the rich solvent in line 155, the aromatics can be about 50% wt, about 60% wt, about 70% wt, about 80% wt, or about 90% wt, with the balance being non-aromatic hydrocarbons. In one or more embodiments, the solvent concentration in the rich solvent in line 155 can range from a low of about 51% wt, about 65% wt, or about 70% wt to a high of about 80% wt, about 85% wt, or about 90% wt.

The rich solvent via line 155 can be introduced to the heat exchanger 445 to transfer heat from the lean solvent introduced via line 462 to provide a heated rich solvent via line 447 and a cooled lean solvent via line 150. The heated rich solvent via line 447 can be introduced to the stripper 410 to provide a less-aromatic rich hydrocarbon via line 412 and a solvent further enriched in aromatic hydrocarbons via line 414.

The raffinate in line 160 can have a non-aromatic hydrocarbon concentration ranging from a low of about 80% wt, about 85% wt, or about 90% wt to a high of about 95% wt, about 97% wt, about 98% wt, or more. In one or more embodiments, the raffinate in line 160 can have an aromatic hydrocarbon concentration ranging from a low of about 0.5% wt, about 1% wt, or about 3% wt to a high of about 5% wt, about 10% wt, or about 20% wt. In one or more embodiments, the raffinate in line 160 can have a solvent concentration ranging from a low of about 0.1% wt, about 0.25% wt, or about 0.5% wt to a high of about 0.75% wt, about 1% wt, or about 2% wt.

The raffinate in line 160 can be introduced to the raffinate wash column 430 to provide a raffinate product lean in solvent (e.g., sulfolane) via line 432 and a recovered water/solvent stream via line 434. The raffinate wash column 430 can separate at least a portion of the solvent in the raffinate to provide a raffinate product via line 432 containing less solvent than the raffinate in line 160. The recovered water/solvent in line 434 can contain aromatics/non-aromatics separated in/entrained from the raffinate wash column 430 from the raffinate introduced via line 160. The recovered water/solvent in line 434 can be introduced to the water stripper 420 to provide a water-lean, hydrocarbon-rich stream via line 422. The non-aromatic rich raffinate via line 432 can be further processed or sent to storage.

The water-lean, hydrocarbon-rich stream in line 422 can be introduced to the water/hydrocarbon separator 470 to provide a recycle hydrocarbon via line 472 and a recovered water stream via line 474. In one or more embodiments, the recycle hydrocarbons via line 472 can be introduced to the first section 120, and/or the second section 130, and/or the third section 140 of the extractor 100 for additional processing. In one or more embodiments, the recycle hydrocarbon via line 472 can be mixed with the feed line 145. It is important to recognize that the internals of column 100 shown in FIG. 1 are merely representative and various other arrangements and designs of the sections are possible.

Within the recovery column 440, the bottoms from the stripper 410 is contacted with steam to recover the aromatics. The aromatic compounds are removed from the top of the recovery column 440 and the bottom stream (lean solvent) 462 may be recycled back to the extractor 100 (line not shown for convenience of view) and/or regenerated in the solvent regenerator 442 and returned to the recovery column 440 via line 443. The overhead from the recovery column 440 is introduced to the water/hydrocarbon separator 465 to separate the water via line 467, which is sent to the water wash column 430, from the product aromatics via line 466. At least a portion of the recovered aromatics can optionally be recycled to the recovery column 440 as reflux, and the product aromatic is recovered at exit point 550, preferably after being analyzed for oxygen content at analyzer 81. The recovered water is sent to the water wash column 430.

FIG. 2 is a basic schematic showing a deaeration tower of the type useful in the present invention. One of skill in the art will appreciate that numerous other types of deaerators may also be useful. Plural trays are shown in FIG. 2 as unnumbered dotted lines within the deaerator column. A stripping gas, e.g., nitrogen, is fed into the bottom of the column to contact the hydrocarbon feed entering into the top of the column, and the hydrocarbon is deaerated in this manner. The deaerated hydrocarbon feed is then pumped to the extractor column, being analyzed for oxygen concentration by one or more devices per se well-known in the art.

FIG. 3 is an apparatus showing the treatment of the hydrocarbon feed to remove chloride and also accomplish the removal of certain non-aromatic species, and is a preferred embodiment of the invention. Chloride treaters for aromatic feedsteams are per se known in the art. See for instance U.S. Pat. Nos. 7,154,014 and 7,307,034; U.S. Publication No. 2007-0086933; and U.S. application Ser. No. 13/183,009.

While the illustrative embodiments of the invention have been described with particularity, it will be understood that various other modifications will be apparent to and can be readily made by those skilled in the art without departing from the spirit and scope of the invention.

Trade names used herein are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated.

What is claimed is:

1. In a method for separating aromatic compounds from a hydrocarbon mixture, including providing a feed comprising one or more solvents and a hydrocarbon mixture comprising one or more aromatic compounds and one or more non-aromatic compounds to a liquid-liquid extractor or liquid-vapor extractor and recovering an extract comprising a majority of aromatic compounds, said extractor having a circulating solvent, recovering a raffinate comprising a majority of the non-aromatics and recovering a rich solvent comprising a majority of the aromatics, wherein said rich solvent is subsequently separated in two streams, a first stream comprising a majority of the solvent and a second stream comprising a majority of the aromatics, wherein said solvent is recycled, the improvement comprising limiting the molecular oxygen content of said feed and/or said circulating solvent to less than 0.1 vppm (as $O_2$), and the amount of organic chlorides in said feed and/or said circulating solvent to less than 0.1 wppm (as Chloride).

2. The process of claim 1, wherein said circulating solvent is filtered through filter elements of 1.0 micron or less, said solvent has a chloride (Cl-) concentration of less than 25 wppm, and said circulating solvent has a chloride content of less than 0.1 wppm.

3. The process of claim 1, wherein said circulating solvent has a TAN (comprising both free acid and acid salts) of less than 1 meq/L (mili-equivalent per Liter).

4. The process of claim 1, wherein said extract has a molecular oxygen content of less than 0.1 vppm.

5. The process of claim 1, wherein said solvent and water pH are maintained between 6-9.

6. The process of claim 1, wherein said solvent is tetrahydrothiophene-1,1-dioxide.

\* \* \* \* \*